United States Patent
Davis et al.

(10) Patent No.: US 11,672,820 B2
(45) Date of Patent: *Jun. 13, 2023

(54) OPHTHALMIC COMPOSITIONS WITH IMPROVED DESSICATION PROTECTION AND RETENTION

(71) Applicant: Alcon Inc., Fribourg (CH)

(72) Inventors: James W. Davis, Falmouth, ME (US); Howard Allen Ketelson, Dallas, TX (US); Elaine E. Campbell, Shelton, CT (US); David L. Meadows, Colleyville, TX (US); Rekha Rangarajan, Fort Worth, TX (US)

(73) Assignee: Alcon Inc., Fribourg (CH)

( * ) Notice: Subject to any disclaimer, the term of this patent is extended or adjusted under 35 U.S.C. 154(b) by 0 days.

This patent is subject to a terminal disclaimer.

(21) Appl. No.: 17/664,143

(22) Filed: May 19, 2022

(65) Prior Publication Data

US 2022/0273699 A1 Sep. 1, 2022

Related U.S. Application Data

(63) Continuation of application No. 17/060,343, filed on Oct. 1, 2020, now Pat. No. 11,376,275, which is a continuation of application No. 16/721,443, filed on Dec. 19, 2019, now Pat. No. 10,828,320, which is a continuation of application No. 15/421,513, filed on Feb. 1, 2017, now abandoned, which is a continuation of application No. 13/886,788, filed on May 3, 2013, now abandoned.

(60) Provisional application No. 61/642,901, filed on May 4, 2012.

(51) Int. Cl.
| | |
|---|---|
| *A61K 31/736* | (2006.01) |
| *A61K 9/00* | (2006.01) |
| *A61K 47/02* | (2006.01) |
| *A61K 47/10* | (2017.01) |
| *A61K 47/26* | (2006.01) |
| *A61K 47/36* | (2006.01) |
| *A61K 47/32* | (2006.01) |
| *A61K 31/728* | (2006.01) |

(52) U.S. Cl.
CPC .......... *A61K 31/736* (2013.01); *A61K 9/0048* (2013.01); *A61K 31/728* (2013.01); *A61K 47/02* (2013.01); *A61K 47/10* (2013.01); *A61K 47/26* (2013.01); *A61K 47/32* (2013.01); *A61K 47/36* (2013.01)

(58) Field of Classification Search
None
See application file for complete search history.

*Primary Examiner* — Dale R Miller
(74) *Attorney, Agent, or Firm* — Sheng-Hsin Hu

(57) ABSTRACT

The present invention relates to artificial tear compositions and ophthalmic compositions suitable for drug delivery. In one embodiment of the present invention, the compositions comprise a galactomannan polymer such as guar or hydroxypropyl guar, hyaluronic acid, and a cis-diol such as sorbitol. In a preferred embodiment, the compositions also comprise a borate compound.

12 Claims, 4 Drawing Sheets

OPHTHALMIC COMPOSITIONS WITH IMPROVED DESSICATION PROTECTION AND RETENTION

This application is a continuation of U.S. patent application Ser. No. 17/060343 filed 01 Oct. 2020, which is a continuation of U.S. patent application Ser. No. 16/721443 filed 19 Dec. 2019, now U.S. Ser. No. 10,828,320, which is a continuation of U.S. patent application Ser. No. 15/421,513 filed 01 Feb 2017, now abandoned; which is a continuation of U.S. patent application Ser. No. 13/886,788 filed 03 May 2013, now abandoned; which application claimed priority to provisional application Ser. No. 61/642,901, filed 04 May 2012, incorporated herein by reference in its entirety.

CROSS-REFERENCE TO RELATED APPLICATION

Technical Field of the Invention

The present invention relates to artificial tear compositions and compositions for ophthalmic drug delivery, and more specifically to compositions comprising a galactomannan such as guar, hyaluronic acid, and a cis-diol.

Background of the Invention

Ophthalmic compositions for topical application, and in particular artificial tear compositions, comprise compounds that lubricate and protect the ocular surface. In the context of dry eye disorders, artificial tear compositions can prevent symptoms such as pain and discomfort and can prevent bioadhesion and tissue damage induced by friction. A large number of potential compounds are available that are useful as lubricants and ocular surface protectants. For example, certain marketed artificial tear products contain natural polymers such as galactomannans. Other lubricants and ocular surface protectants include, for example, carboxymethylcellulose, glucomannan, glycerol, and hydroxypropylmethylcellulose.

As noted above, ophthalmic compositions have been previously described that utilize galactomannan compounds such as guar. U.S. Pat. No. 6,403,609 to Asgharian, entitled "Ophthalmic compositions containing galactomannan polymers and borate," describes such systems and is herein incorporated by reference in its entirety.

Though existing artificial tear compositions have met with some success, problems in the treatment of dry eye nevertheless remain. The use of tear substitutes, while temporarily effective, generally requires repeated application over the course of a patient's waking hours. It is not uncommon for a patient to have to apply artificial tear solution ten to twenty times over the course of the day. Such an undertaking is not only cumbersome and time consuming, but, is also potentially very expensive. Transient symptoms of dry eye associated with refractive surgery have been reported to last in some cases from six weeks to six months or more following surgery.

BRIEF SUMMARY OF THE INVENTION

The present invention relates to ophthalmic dry eye compositions comprising guar and hyaluronic acid. A cis-diol, such as sorbitol or propylene glycol, is also present in the compositions. In certain embodiments, a borate compound is also present in the compositions. The compositions of the invention provide improved desiccation protection and retention characteristics. The compositions of the present invention are also useful as drug delivery vehicles for ophthalmic therapeutics, The present inventors have discovered that the combination of guar and hyaluronic acid demonstrates a synergistic effect relative to desiccation protection and ocular surface retention when compared to compositions containing either polymer alone.

Furthermore, the compositions of the present invention demonstrated improved stability when subjected to elevated temperatures such as those encountered during sterilization processes such as autoclaving.

The foregoing brief summary broadly describes the features and technical advantages of certain embodiments of the present invention. Additional features and technical advantages will be described in the detailed description of the invention that follows.

BRIEF DESCRIPTION OF THE DRAWINGS

A more complete understanding of the present invention and the advantages thereof may be acquired by referring to the following description, taken in conjunction with the figures of the accompanying drawing in which like reference numbers indicate like features and wherein.

DETAILED DESCRIPTION OF THE INVENTION

Figure 1:
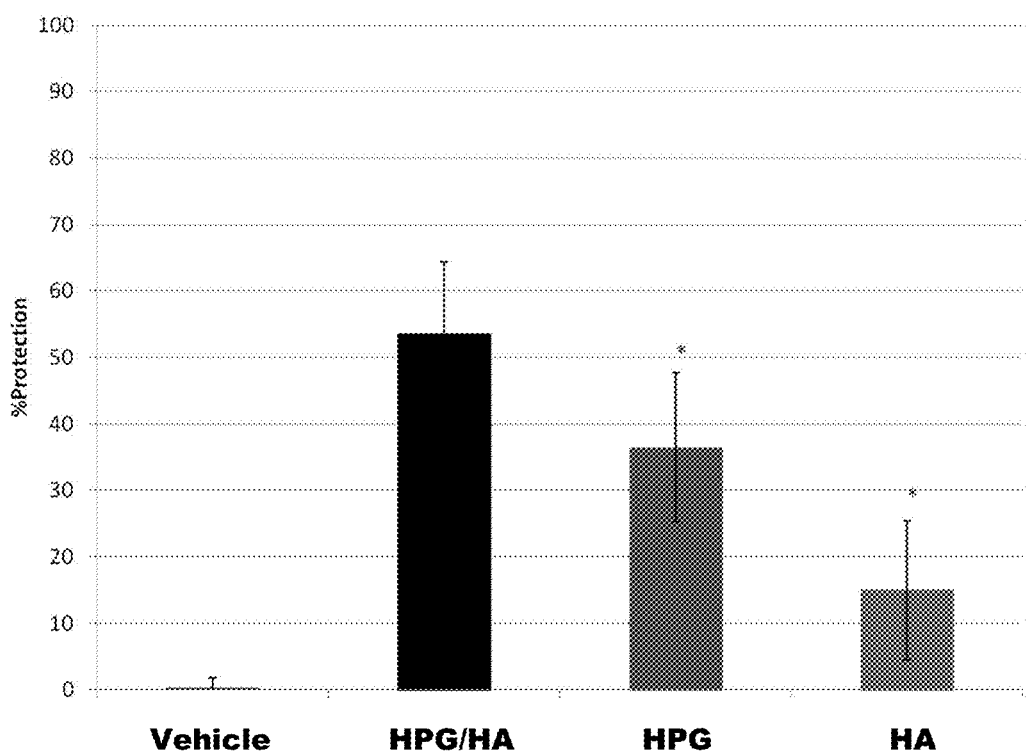
FIG. 1 is a bar chart comparing desiccation performance of a composition comprising both hydroxypropyl guar and hyaluronic acid to compositions comprising to either hydroxypropyl guar or hyaluronic acid.

The compositions of the present invention comprise a galactomannan such as guar, hyaluronic acid, and a cis-diel. The types of galactomannans that may be used in the present invention are typically derived from guar gum, locust bean gum and tara gum. As used herein, the term "galactomannan" refers to polysaccharides derived from the above natural gums or similar natural or synthetic gums containing mannose or galactose moieties, or both groups, as the main structural components. Preferred galactomannans of the present invention are made up of linear chains of (1-4)-β-D-mannopyranosyl units with α-D-galactopyranosyl units attached by (1-6) linkages. With the preferred galactomannans, the ratio of D-galactose to D-mannose varies, but generally will be from about 1:2 to 1:4. Galactomannans having a D-galactose:D-mannose ratio of about 1:2 are most preferred. Additionally, other chemically modified variations of the polysaccharides are also included in the "galactomannan" definition. For example, hydroxyethyl, hydroxypropyl and carboxymethylhydroxypropyl substitutions may be made to the galactomannans of the present invention. Non-ionic variations to the galactomannans, such as those containing alkoxy and alkyl (C1-C6) groups are particularly preferred when a soft gel is desired (e.g., hydroxylpropyl substitutions). Substitutions in the non-cis hydroxyl positions are most preferred. An example of non-ionic substitution of a galactomannan of the present invention is hydroxypropyl guar, with a molar substitution of about 0.4. Anionic substitutions may also be made to the galactomannans. Anionic substitution is particularly preferred when strongly responsive gels are desired. A galactomannan is typically present in a composition of the present invention at a concentration of about 0.025 to about 0.8 w/v %, preferably at about 0.1 w/v %4 to about 0.2 w/v %, and more preferably at about 0.17 to about 0.18 w/v %. In one embodiment, hydroxypropyl guar is present at a concentration of about 0.175 w/v %. Preferred galactomannans of the present invention are guar and hydroxypropyl guar. Hydroxypropyl guar is particularly preferred.

Glycosaminoglycans such as hyaluronic acid are negatively charged molecules. Hyaluronic acid is an unsulphated glycosaminoglycan composed of repeating disaccharide units of N-acetylglucosamine (GlcNAc) and glucuronic acid (GlcUA) linked together by alternating beta-1,4 and beta-1,3 glycosidic bonds. Hyaluronic acid is also known as hyaluronan, hyaluronate, or HA. As used herein, the term hyaluronic acid also includes salt forms of hyaluronic acid such as sodium hyaluronate. Compositions of the present invention comprise from about 0.05 to about 0.5 w/v % hyaluronic acid. In a preferred embodiment, hyaluronic acid is present at a concentration of about 0.1 to about 0.2 w/v %, and more preferably at a concentration of about 0.13 to 0.17 w/v %. Ii one embodiment, sodium hyaluronate is present at a concentration of about 0.15 w/v %. A preferred hyaluronic acid is sodium hyaluronate. The molecular weight of the hyaluronic acid used in compositions of the present invention may vary, but is typically 0.5 to 2.0 M Daltons. In one embodiment, the hyaluronic acid has a molecular weight of 900.000 to 1M Daltons. In another embodiment, the hyaluronic acid has a molecular weight of 1.9 to 2.0 M Daltons.

The cis-diol compounds that may be used with embodiments of the present invention include, but are not limited to, hydrophilic carbohydrates such as sorbitol or mannitol that comprise cis-diol groups (hydroxyl groups attached to adjacent carbon atoms). Preferred cis-diol compounds of the present invention include polyethylene glycols, polypropylene glycols, and polyethyleneoxide-polybutyleneoxide block copolymers. Particularly preferred cis-diol compounds are sorbitol and mannitol. The cis-diol compounds are present at concentrations of about 0.5 to 5.0 w/v % in the compositions of the present invention, and are preferably present at a concentration of about 1.0 to 2.0 w/v %. In one embodiment, sorbitol is present at a concentration of about 1.4%. Generally, the molecular weight of such cis-diol compounds is between 400 g/mol to 5 million g/mol.

When present in a composition of the present invention, borate is typically at a concentration of about 0.1 to about 1.8 w/v %. In a preferred embodiment, borate is present at a concentration of 0.3 to 0.4 w/v %. In one embodiment of the present invention, boric acid is present at a concentration of about 0.35 w/v %. As used herein, the term "borate" refers to all pharmaceutically suitable forms of borates, including but not limited to boric acid, and alkali metal borates such as sodium borate and potassium borate. Boric acid is the preferred borate used with embodiments of the present invention.

The compositions of the present invention may optionally comprise one or more additional excipients and/or one or more additional active ingredients. Excipients commonly used in pharmaceutical compositions include, but are not limited to, demulcents, tonicity agents, preservatives, chelating agents, buffering agents, and surfactants. Other excipients comprise solubilizing agents, stabilizing agents, comfort-enhancing agents, polymers, emollients, pH-adjusting agents and/or lubricants. Any of a variety of excipients may be used in compositions of the present invention including water, mixtures of water and water-miscible solvents, such as C1-C7-alkanols, vegetable oils or mineral oils comprising from 0.5 to 5% non-toxic water-soluble polymers, natural products, such as alginates, pectins, tragacanth, karaya gum, xanthan gum, carrageenin, agar and acacia, starch derivatives, such as starch acetate and hydroxypropyl starch, and also other synthetic products such as polyvinyl alcohol, polyvinylpyrrolidone, polyvinyl methyl ether, polyethylene oxide, preferably cross-linked polyacrylic acid and mixtures of those products, Demulcents used with embodiments of the present invention include, but are not limited to, glycerin, polyvinyl pyrrolidone, polyethylene oxide, polyethylene glycol, propylene glycol and polyacrylic acid. Particularly preferred demulcents are propylene glycol and polyethylene glycol 400.

Suitable tonicity-adjusting agents include, but are not limited to, mannitol, sodium chloride, glycerin, and the like. Suitable buffering agents include, but are not limited to, phosphates, acetates and the like, and amino alcohols such as 2-amino-2-methyl-1-propanol (AMP). Suitable surfactants include, but are not limited to, ionic and nonionic surfactants, though nonionic surfactants are preferred, RLM 100, POE 20 cetylstearyl ethers such as Procol® CS20 and poloxamers such as Pluronic® F68.

The compositions set forth herein may comprise one or more preservatives. Examples of such preservatives include p-hydroxybenzoic acid ester, sodium perborate, sodium chlorite, alcohols such as chlorobutanol, benzyl alcohol or phenyl ethanol, guanidine derivatives such as polyhexamethylene biguanide, sodium perborate, polyquaternium-1, or sorbic acid. In certain embodiments, the composition may be self-preserved so that no preservation agent is required.

Compositions of the present invention are ophthalmically suitable for application to a subject's eyes. The term "aqueous" typically denotes an aqueous composition wherein the excipient is >50%, more preferably >75% and in particular >90% by weight water. These drops may be delivered from a single dose ampoule which may preferably be sterile and thus render bacteriostatic components of the composition unnecessary. Alternatively, the drops may be delivered from a multi-dose bottle which may preferably comprise a device which extracts any preservative from the composition as it is delivered, such devices being known in the art.

The compositions of the present invention are preferably isotonic, or slightly hypotonic in order to combat any hypertonicity of tears caused by evaporation and/or disease. This may require a tonicity agent to bring the osmolality of the composition to a level at or near 210-320 milliosmoles per kilogram (mOsm/kg). The compositions of the present invention generally have an osmolality in the range of 220-320 mOsm/kg, and preferably have an osmolality in the range of 235-300 mOsm/kg. The ophthalmic compositions will generally be formulated as sterile aqueous solutions.

The compositions of the present invention can also be used to administer pharmaceutically active compounds for the treatment of, for example, ophthalmic diseases such as glaucoma, macular degeneration, and ocular infections. Such compounds include, but are not limited to, glaucoma therapeutics, pain relievers, anti-inflammatory and anti-allergy medications, and anti-microbials. More specific examples of pharmaceutically active compounds include betaxolol, timolol, pilocarpine, carbonic anhydrase inhibitors and prostaglandins; dopaminergic antagonists; post-surgical antihypertensive agents, such as para-amino clonidine (apraclonidine); anti-infectives such as ciprofloxacin, moxifloxacin, and tobramycin; non-steroidal and steroidal anti-inflammatories, such as naproxen, diclofenac, nepafenac, suprofen, ketorolac, tetrahydrocortisol and dexamethasone; dry eye therapeutics such as PDE4 inhibitors; and anti-allergy medications such as H1/H4 inhibitors. H4 inhibitors, and olopatadine.

It is also contemplated that the concentrations of the ingredients comprising the compositions of the present invention can vary. A person of ordinary skill in the art would understand that the concentrations can vary depending on the addition, substitution, and/or subtraction of ingredients in a given composition.

Preferred compositions are prepared using a buffering system that maintains the composition at a pH of about 6.5 to a pH of about 8.0. Topical compositions (particularly topical ophthalmic compositions, as noted above) are preferred which have a physiological pH matching the tissue to which the composition will be applied or dispensed.

In particular embodiments, a composition of the present invention is administered once a day. However, the compositions may also be formulated for administration at any frequency of administration, including once a week, once every 5 days, once every 3 days, once every 2 days, twice a day, three times a day, four times a day, five times a day, six times a day, eight times a day, every hour, or greater frequency. Such dosing frequency is also maintained for a varying duration of time depending on the therapeutic regimen. The duration of a particular therapeutic regimen may vary from one-time dosing to a regimen that extends for months or years. One of ordinary skill in the art would be familiar with determining a therapeutic regimen for a specific indication.

The following examples are presented to further illustrate selected embodiments of the present invention.

Example 1

| Ingredient | % W/V |
| --- | --- |
| Hydroxypropyl Guar | 0.025 to 0.8 |
| Sodium Hyaluronate | 0.13 to 0.17 |
| Boric Acid | 0.35 |
| Sorbitol | 1.4 |
| PEG 400 | 0.4 |
| EDTA Sodium | 0.025 |
| Propylene Glycol | 0.3 |
| Potassium Chloride | 0.12 |
| Sodium Chloride | 0.1 |
| Polyquaternium-1 | 0.001 + 10% excess |
| 2-Amino-2-methylpropanol | 0.27 |
| Sodium Hydroxide/Hydrochloric Acid | q.s. pH 7.9 |
| Purified Water | q.s. 100% |

Example 2

Guar and hyaluronate compositions of the present invention were autoclaved under standard conditions. As shown below in Table 1, the composition comprising sorbitol has a stabilized molecular weight when compared with the composition that did not contain sorbitol.

TABLE 1

| Sodium Hyaluronate | [HA] Powder | [HA] alone | [HA] with Sorbitol |
| --- | --- | --- | --- |
| Initial (Powder, $1 \times 10^6$ g/mol) | 1.7 (PD = 1.5) | — | — |
| Molecular Weight Before autoclave ($1 \times 10^6$ g/mol) | — | 1.9 (PD = 1.4) | 1.9 (PD = 1.5) |
| Molecular Weight After Autoclave ($1 \times 10^6$ g/mol) | — | 0.4 (PD = 1.6) | 1.4 (PD = 1.3) |
| pH before Autoclave | — | 7.0 | 7.0 |
| pH after Autoclave | — | 6.5 | 6.8 |
| Viscosity at $0.1\ s^{-1}$ Before Autoclave | — | 241 | 249 |
| Viscosity at $10\ s^{-1}$ After Autoclave | — | 24 | 96 |

Example 3

The ability of compositions of the present invention to protect human epithelial cells from desiccating stress was evaluated as follows. Human transformed corneal epithelial cells were plated at $0.09 \times 10^5$ ells/mL onto collagen-coated 48-well plates (BD Biosciences #35-4505) and grown to confluence in Epilife media (Invitrogen #MEPIS00CA) supplemented with Human Corneal Growth Supplement (HCGS Invitrogen #S0095) for 48 hours. Cells were treated with test solutions for 30 minutes at 37° C. then rinsed IX (250 µL) with supplement free media. All solutions were gently removed and the cells were subjected to desiccation at 45% humidity, 37° C. for 30 minutes in a desiccation chamber (Caron Environmental Chamber 6010 Series). Cellular viability was determined using an MTS assay (Promega 1, G5421) to as calculate % protection relative to media control. An assessment of solution cell surface retention was conducted by modifying the above desiccation experiment whereby five "media washes" were performed after the 30 minute test solution incubation. Among the test solutions were a hydroxypropyl guar composition (HPG), a hyaluronic acid composition (HA), and a composition of the present invention comprising both hydroxypropyl guar and hyaluronic acid (HPG/IA).

Figure 2:
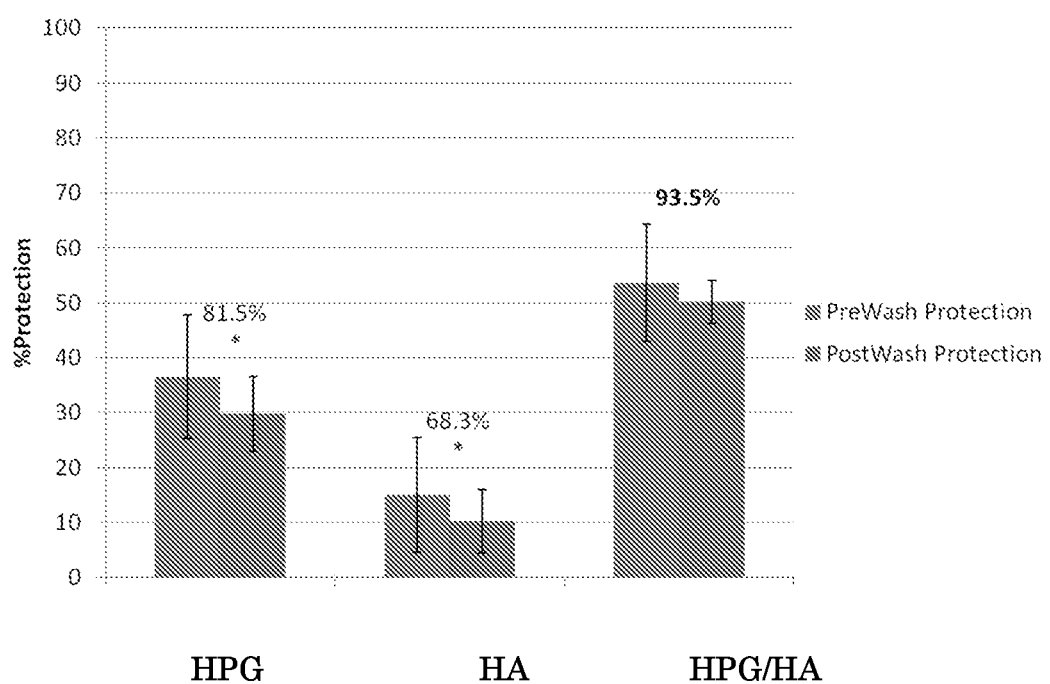
FIG. 2 is a is a bar chart comparing retention performance of a composition comprising hydroxypropyl guar and hyaluronic acid to compositions comprising hydroxypropyl guar and hyaluronic avid alone.

Referring to FIG. 1 and TABLES 2 and 3 below, the DPS composition demonstrated significantly greater desiccation protection than either the HPG solution or the HA solution. As shown in FIG. 2 and TABLE 3, the HPG/HA solution also demonstrated greater retention to the epithelial surface than either the HPG solution or the HA solution. A synergistic effect was noted relative to both desiccation protection and retention behavior of the HPG/HA solution.

TABLE 2

| Ingredient | Hydroxypropyl Guar (HPG) (% W/V) | Hylaruronic Acid (HA) (% W/V) | Hydroxypropyl Guar/Hyaluronic Acid (HPG/HA) (% W/V) |
| --- | --- | --- | --- |
| Hydroxypropyl Guar | 0.175 | — | 0.175 |
| Sodium Hyaluronate | — | 0.15 | 0.15 |
| Sodium Citrate, Dihydrate | 0.6 | 0.6 | 0.6 |
| Sorbitol | 1.4 | 1.4 | 1.4 |
| Polyethylene Glycol 400 | 0.4 | 0.4 | 0.4 |
| Propylene Glycol | 0.3 | 0.3 | 0.3 |
| AMP-Ultra | 0.27 | 0.27 | 0.27 |
| Boric Acid | 0.18 | 0.18 | 0.18 |
| Sodium Borate, Decahydrate | 0.262 | 0.262 | 0.262 |

TABLE 2-continued

| Ingredient | Hydroxypropyl Guar (HPG) (% W/V) | Hylaruronic Acid (HA) (% W/V) | Hydroxypropyl Guar/Hyaluronic Acid (HPG/HA) (% W/V) |
|---|---|---|---|
| Sodium Chloride | 0.07 | 0.07 | 0.07 |
| Disodium EDTA | 0.025 | 0.025 | 0.025 |
| Potassium Chloride | 0.12 | 0.12 | 0.12 |
| Polyquaternium-1 | 0.001 | 0.001 | 0.001 |
| pH | 7.9 | 7.9 | 7.9 |
| Purified Water | QS | QS | QS |
| Desiccation Protection (%) | 47 ± 12 | 5 ± 5 | 56 ± 13[a] |
| Retention Protection (%) | 36 ± 12 | 5 ± 9 | 43 ± 12[b] |

[a, b] $p < 0.05$: Statistical significance based on one-way ANOVA relative to HPG and HA alone.

TABLE 3

| | BORATE BUFFERED | |
|---|---|---|
| Ingredient | Hydroxypropyl Guar (HPG) (W/V %) | Hydroxypropyl Guar/Hyaluronic Acid (HPG/HA) (W/V %) |
| Hydroxypropyl Guar | 0.17 | 0.17 |
| Hyaluronic Acid | — | 0.15 |
| Sodium Chloride | 0.66 | 0.66 |
| Sodium Phosphate, Dibasic Anhydrous | — | — |
| Potassium Chloride | — | — |
| Boric Acid | 0.5 | 0.5 |
| Sodium Borate, Decahydrate | 0.052 | 0.052 |
| Purified Water | QS | QS |
| pH | 7.5 | 7.5 |
| Desiccation Protection (%) | 64.8 ± 7.0 | 77.0 ± 6.2[c] |
| Retention Protection (%) | 52.9 ± 13.3 | 59.3 ± 13.4[d] |

[c, d] $p < 0.05$: Statistical significance based on one-way ANOVA relative to HPG alone.

Figure 3:
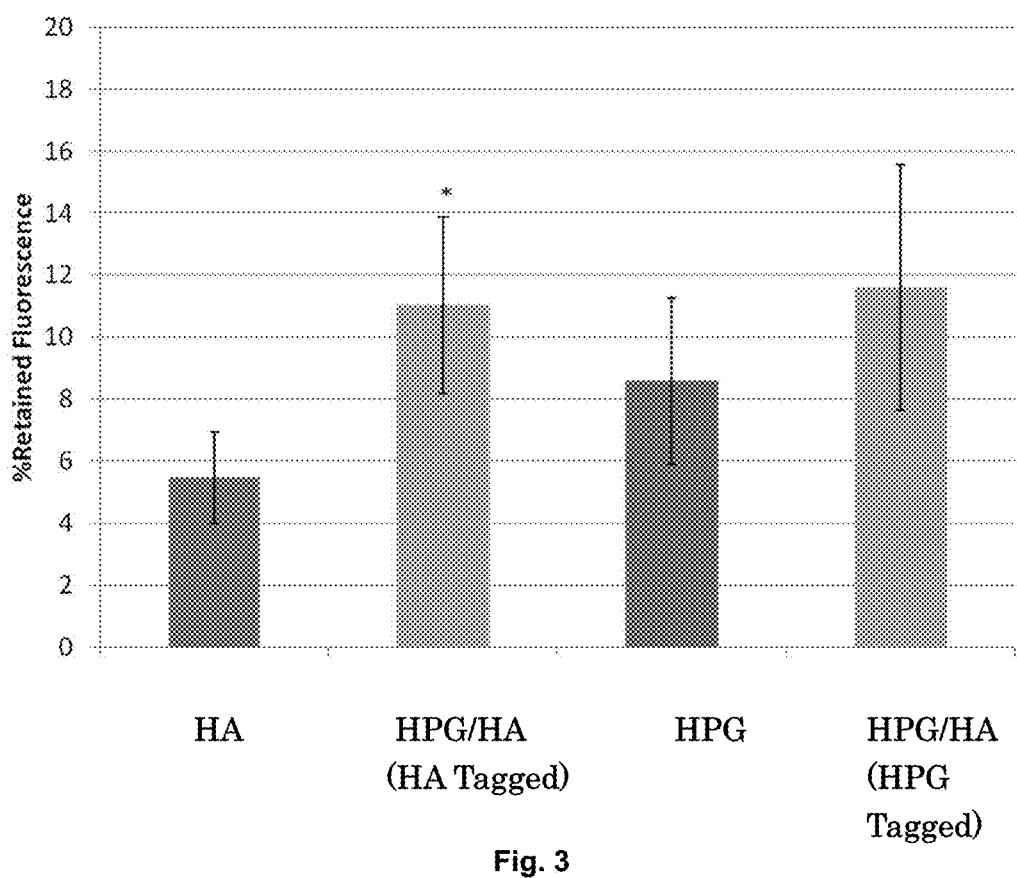
FIG. 3 is a bar chart comparing retention of fluorescently-tagged polymer compositions.
Figure 4:
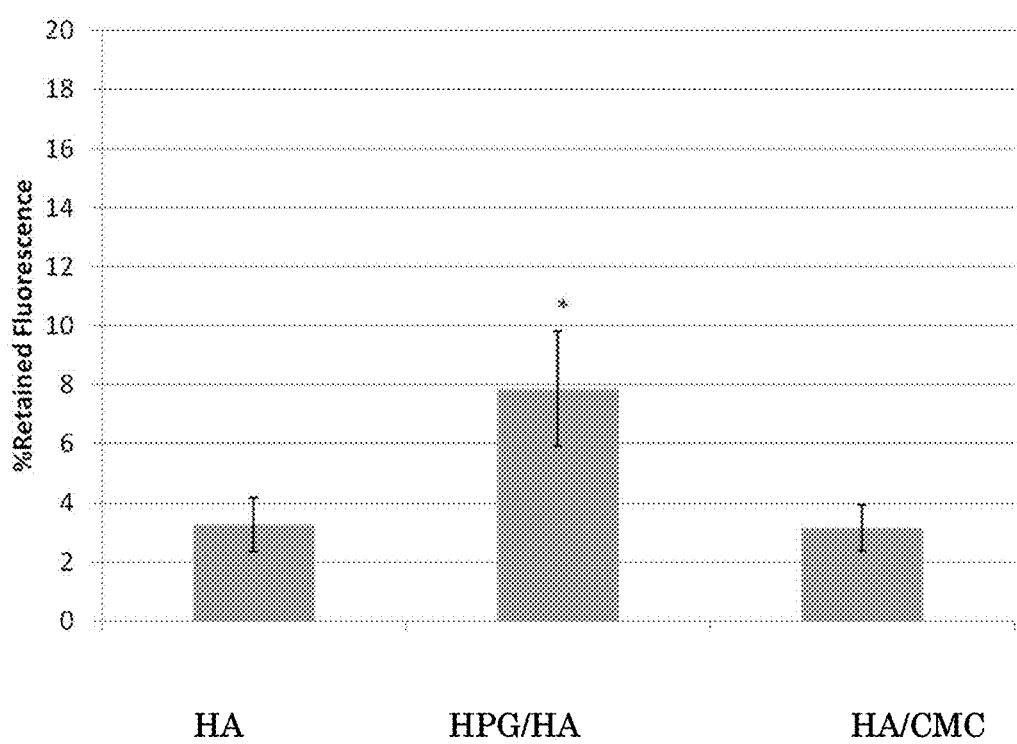
FIG. 4 is a bar chart comparing retention of a hydroxypropyl guar/hyaluronic acid composition with a hyaluronic acid/carboxymethylcellulose composition.

The mean retention time of a composition of the present invention was compared to its components alone. Briefly, a fluorescein labeled dextran tracer of approximately 70 kD (Molecular Probes, Eugene. Oreg.) was added to each test formulation at a concentration of 0.1 w/v %. A scanning fluorophotometer (Ocumetrics, Mountain View, Calif.) was used to monitor signal decay corresponding to elimination of the formulations. As shown in FIG. 3 and TABLE 4 below, individual fluorescent tagging of the polymer components of the HPG/HA solution demonstrates an increase in the amount of polymer bound to the epithelial surface when the polymers hydroxypropyl guar and hyaluronic acid are combined. FIG. 4 and TABLE 5 demonstrate that this improved retention effect was not noted in a dual polymer formulation comprising hyaluronic acid and carboxymethylcellulose (HA/CMC).

TABLE 4

| Compositions | Fluorescent Tag | % Retained Fluorescence |
|---|---|---|
| Hyaluronic Acid (HA) | Sodium Fluorescein | 5.46 ± 1.46 |
| HydroxyPropyl Guar/Hyaluronic Acid (HPG/HA) | Sodium Fluorescein | 11.03 ± 2.85[e] |
| HydroxyPropyl Guar (HPG) | Texas Red | 8.58 ± 2.69 |
| HydroxyPropyl Guar/Hyaluronic Acid (HPG/HA) | Texas Red | 11.60 ± 3.96 |

[e] $p < 0.05$: Statistical significance based on one-way ANOVA relative to HA alone.

TABLE 5

| Compositions | Fluorescent Tag | % Retained Fluorescence |
|---|---|---|
| Hyaluronic Acid (HA) | Sodium Fluorescein | 3.25 ± 0.91 |
| Hydroxypropyl Guar/Hyaluronic Acid (HPG/HA) | Sodium Fluorescein | 7.85 ± 1.94[f] |
| Hyaluronic Acid/Carboxymethyl cellulose (HA/CMC) | Sodium Fluorescein | 3.17 ± 0.78 |

[f] $p < 0.05$: Statistical significance based on one-way ANOVA relative to HA alone and HA/CMC compositions.

Referring to TABLE 6, which presents data comparing the desiccation and retention performance of marketed dry eye compositions comprising hyaluronic acid, the HPG/HA composition demonstrated significantly greater desiccation protection and retention of effect relative to the currently marketed HA products tested.

TABLE 6

| Formulations | Desiccation Protection (%) | Retention Protection (%) |
|---|---|---|
| Blink Tears | 10 ± 7 | 3 ± 7 |
| Blink Gel Tears | 25 ± 8 | 7 ± 10 |
| HPG/HA | 57 ± 13[g] | 43 ± 12[h] |

[g, h] $p < 0.05$: Statistical significance based on one-way ANOVA relative to marketed HA products.

TABLE 7 presents the results of a hyaluronic acid dose response study which compares the desiccation protection of compositions with hyaluronic acid alone to compositions comprising hyaluronic acid and hydroxypropyl guar.

TABLE 7

| Ingredient | Hydroxypropyl Guar/Hyaluronic Acid (W/V %) | | | Hyaluronic Acid (W/V %) | | |
|---|---|---|---|---|---|---|
| Hydroxypropyl Guar (HPG) | 0.175 | 0.175 | 0.175 | — | — | — |
| Sodium Hyaluronate | 0.01 | 0.05 | 0.15 | 0.01 | 0.05 | 0.15 |
| Sodium Citrate | 0.6 | 0.6 | 0.6 | 0.6 | 0.6 | 0.6 |
| AMP-Ultra | 0.27 | 0.27 | 0.57 | 0.27 | 0.27 | 0.57 |
| Sorbitol | 1.4 | 1.4 | 1.4 | 1.4 | 1.4 | 1.4 |
| Boric Acid | 0.35 | 0.35 | 0.7 | 0.35 | 0.35 | 0.7 |
| PEG 400 | 0.4 | 0.4 | 0.4 | 0.4 | 0.4 | 0.4 |
| Propylene Glycol | 0.3 | 0.3 | 0.3 | 0.3 | 0.3 | 0.3 |
| Potassium Chloride | 0.12 | 0.12 | 0.12 | 0.12 | 0.12 | 0.12 |
| Sodium Chloride | 0.1 | 0.1 | 0.2 | 0.1 | 0.1 | 0.2 |

TABLE 7-continued

| Ingredient | Hydroxypropyl Guar/ Hyaluronic Acid (W/V %) | | | Hyaluronic Acid (W/V %) | | |
| --- | --- | --- | --- | --- | --- | --- |
| EDTA | 0.025 | 0.025 | 0.025 | 0.025 | 0.025 | 0.025 |
| Polyquaternium-1 | 0.001 | 0.001 | 0.001 | 0.001 | 0.001 | 0.001 |
| Purified Water | QS | QS | QS | QS | QS | QS |
| pH | 7.89 | 7.91 | 7.90 | 7.92 | 7.88 | 7.89 |
| Desiccation Protection (%) | 39.49 ± 8.53[1] | 40.28 ± 7.77[1] | 45.33 ± 9.02[1] | 0.89 ± 2.34 | 0.83 ± 3.31 | 2.38 ± 3.61 |

[1]$p < 0.05$: Statistical significance based on one-way ANOVA relative to HA alone.

The present invention and its embodiments have been described in detail. However, the scope of the present invention is not intended to be limited to the particular embodiments of any process, manufacture, composition of matter, compounds, means, methods, and/or steps described in the specification. Various modifications, substitutions, and variations can be made to the disclosed material without departing from the spirit and/or essential characteristics of the present invention. Accordingly, one of ordinary skill in the art will readily appreciate from the disclosure that later modifications, substitutions, and/or variations performing substantially the same function or achieving substantially the same result as embodiments described herein may be utilized according to such related embodiments of the present invention. Thus, the following claims are intended to encompass within their scope modifications, substitutions, and variations to processes, manufactures, compositions of matter, compounds, means, methods, and/or steps disclosed herein.

The invention claimed is:

1. An ophthalmic composition comprising 0.1 to 0.2 w/v % hydroxylpropyl guar, 0.13 to 0.17 w/v % hyaluronic acid, 1.0 to 2.0 w/v % cis-diol and a pharmaceutically active compound, wherein the cis-diol is sorbitol and the pharmaceutically active compound is selected from the group consisting of a glaucoma therapeutic, a pain reliever, an anti-inflammatory medication, an anti-allergy medication, a post- surgical antihypertensive agent, a dry eye therapeutic, an anti-infective, and an anti-microbial, for the treatment of ophthalmic diseases.

2. The ophthalmic composition according to claim 1 comprising 0.17 to 0.18 w/v % hydroxylpropyl guar, 0.13 to 0.17 w/v % sodium hyaluronate and 1.0 to 2.0 w/v % w/v % sorbitol.

3. The ophthalmic composition according to claim 1 further comprising a borate, wherein said borate is boric acid.

4. The ophthalmic composition according to claim 1 further comprising a demulcent selected from the group consisting of: glycerin, polyvinyl pyrrolidone, polyethylene oxide, polyethylene glycol, propylene glycol, polyacrylic acid, and combinations thereof.

5. The ophthalmic composition according to claim 4, wherein said demulcent is propylene glycol, or polyethylene glycol.

6. The ophthalmic composition according to claim 1, wherein the glaucoma therapeutic is betaxolol, timolol, pilocarpine, or a carbonic anhydrase inhibitor.

7. The ophthalmic composition according to claim 1, wherein the post-surgical antihypertensive agent is para-amino clonidine.

8. The ophthalmic composition according to claim 1, wherein the anti-infective medication is ciprofloxacin, moxifloxacin, or tobramycin.

9. The ophthalmic composition according to claim 1, wherein the anti-allergy medication is an H1/H4 inhibitor, an H4 inhibitor, or olopatadine.

10. The ophthalmic composition according to claim 1, wherein the dry eye therapeutic is a PDE4 inhibitor.

11. The ophthalmic composition according to claim 1, wherein the anti-inflammatory medication is naproxen, diclofenac, nepafenac, suprofen, ketorolac, tetrahydrocortisol, or dexamethasone.

12. The ophthalmic composition according to claim 1, wherein the pain reliever is prostaglandin, or a dopaminergic antagonist.

* * * * *